(12) United States Patent
Kralik et al.

(10) Patent No.: US 7,488,833 B2
(45) Date of Patent: Feb. 10, 2009

(54) PROCESS FOR THE ENANTIOSELECTIVE HYDROGENATION OF AMINO ALCOHOLS

(75) Inventors: Joachim Kralik, Darmstadt (DE); Kai Fabian, Wilhelmsfeld (DE); Christoph Mürmann, Reinheim (DE); Norbert Schweickert, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 329 days.

(21) Appl. No.: 10/525,821

(22) PCT Filed: Aug. 1, 2003

(86) PCT No.: PCT/EP03/08513

§ 371 (c)(1),
(2), (4) Date: Feb. 25, 2005

(87) PCT Pub. No.: WO2004/020389

PCT Pub. Date: Mar. 11, 2004

(65) Prior Publication Data
US 2005/0261514 A1    Nov. 24, 2005

(30) Foreign Application Priority Data
Aug. 27, 2002 (DE) ............................... 102 40 025

(51) Int. Cl.
*C07D 333/20* (2006.01)
*C07C 215/00* (2006.01)
(52) U.S. Cl. .................. 549/75; 564/358; 564/354; 549/58
(58) Field of Classification Search ................. 560/170; 564/123, 354, 358; 549/58, 75
See application file for complete search history.

(56) References Cited

FOREIGN PATENT DOCUMENTS

| DE | 4330730 | 9/1993 |
|---|---|---|
| WO | WO 02/04401 | 1/2002 |
| WO | WO 02/055477 | 7/2002 |

OTHER PUBLICATIONS

G. Helmchen et al.: "Houben-Weyl Methods of Organic Chemistry; Additional and Suppl. Vol. to the 4th Ed. vol. E 21 D, Stereoselective Synthesis (pp. 3995-3997, Chapter 2.2.1.2.7)" Nov. 30, 1995, George Thieme Verlag, Stutgart—New York XP002262293, ISBN: 3-13-100114-3.*

G. Helmchen et al.: "Houben-Weyl Methods of Organic Chemistry; Additional and Suppl. Vol. to the 4th Ed. vol. E 21 D, Stereoselective Synthesis (pp. 3955-3957, Chapter 2.2.1.2.7)" Nov. 30, 1995, George Thieme Verlag, Stutgart- New York XP02262293, ISBN: 3-13-100114-3.*

Sakurba et al. "Efficient Asymmetric Hydrogenation of γ-Amino Ketone Hydrochloride Derivatives catalyzed by (2S,4S)-4-Dicyclohexylphosphino-2-diphenylphosphinomethyl-1(N-methylcarbamoyl)-pyrrolidine(MCCPM)-Rhodium Complex", Synlett, Oct. 1992, p. 829.*

Sakurba et al. "Efficient Asymmetric Hydrogenation of β- and γ-Amino Ketone Derivatives leading to practical Synthesis of Fluoxetine and Eprozinol", Chemical Pharmaceutical Bulletin 1995, p. 748.*

G. Helmchen et al.: Houben-Weyl Methods of Organic Chemistry; Additional and Suppl. vol. of the 4th Ed. vol. E 21d, Stereoselective Synthesis (pp. 3955-3957 Chapter 2.3.1.2.7) Nov. 30, 1995.

M. Kitamura et al.: "Homogeneous Asymmetric Hydrogenation of Functionalized Ketones" J.Am. Chem. Soc., Bd. 110, 1998 (pp. 629-631).

* cited by examiner

*Primary Examiner*—Daniel M Sullivan
*Assistant Examiner*—Yate' K Cutliff
(74) *Attorney, Agent, or Firm*—Miller, White, Zelano, Branigan, P.C.

(57) ABSTRACT

A process for the enantioselective preparation of amino alcohols of formula I

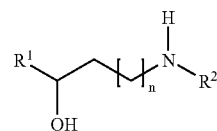

I by enantioselective hydrogenation of amino ketones of the formula II

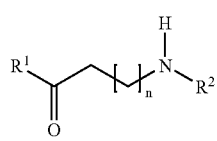

II in the presence of a non-racemic catalyst. The catalyst is a transition-metal complex in which the transition metal is complexed to a chiral diphosphine ligand.

26 Claims, No Drawings

PROCESS FOR THE ENANTIOSELECTIVE HYDROGENATION OF AMINO ALCOHOLS

This application is national stage entry of PCT/EP03/08513 filed Aug. 01-2003, which claims priority to German 10240025 filed Aug. 27 2002.

The invention relates to a process for the enantioselective preparation of amino alcohols of the formula I

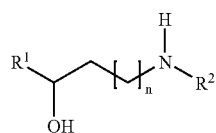

in which
$R^1$ denotes a saturated, unsaturated or aromatic carbocyclic or heterocyclic radical which is unsubstituted or mono- or polysubstituted by $R^3$ and/or $R^4$,
$R^2$ denotes alkyl having 1-20 C atoms or H,
$R^3$, $R^4$ each, independently of one another, denote H, alkyl or alkoxy having 1-20 C atoms, aryl, aryloxy or $COOR^2$, F, Cl, Br, OH, CN, $NO_2$, $N(R^2)_2$ or $NHCOR_2$
and
n denotes 0, 1, 2 or 3, by enantioselective hydrogenation of amino ketones of the formula II

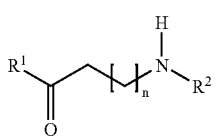

in which
$R^1$, $R^2$ and n have the meaning indicated above, in the presence of a non-racemic catalyst, characterised in that the catalyst is a transition-metal complex in which the transition metal is complexed to a chiral diphosphine ligand A

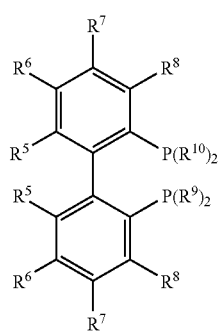

in which
$R^5$, $R^6$, $R^7$ and $R^8$ each, independently of one another, denote H, alkyl or alkoxy having 1-20 C atoms, aryl, aryloxy or F, Cl, Br, $N(R^2)_2$ or $NHCOR_2$
$R^9$ and $R^{10}$ each, independently of one another, denote

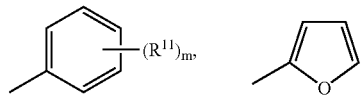

or cyclohexyl $R^{11}$ denotes H, alkyl or alkoxy having 1-20 C atoms, aryl, aryloxy or $SO_3Na$, $COOR^{12}$, F, Cl, $N(R^{12})_2$ or $NHCOR^{12}$,
$R^{12}$ denotes alkyl having 1-20 C atoms or H
and
m denotes 0, 1, 2 or 3, where $R^5$ and $R^6$, $R^6$ and $R^7$ and $R^7$ and $R^8$ together can also have the meaning

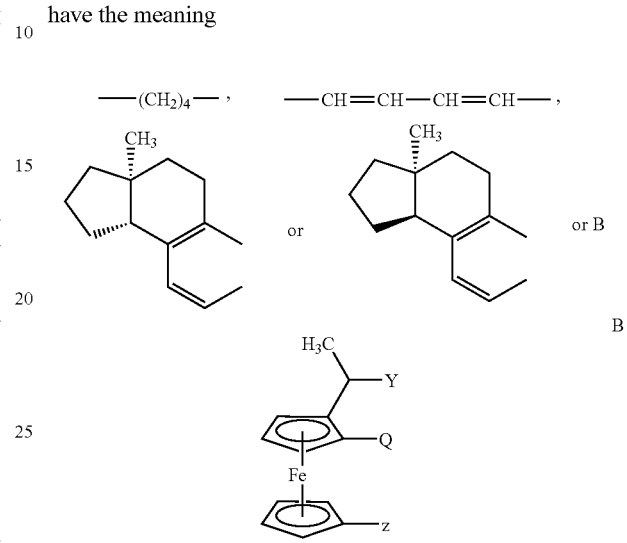

in which
Y denotes OH, P(cyclohexyl)$_2$, P(3,5-dimethylphenyl)$_2$ or P(C(CH$_3$)$_3$)$_2$,
Z denotes H or P(phenyl)$_2$,
Q denotes PPh$_2$, P(cyclohexyl)$_2$, P[3,5-bis(trifluoromethyl)phenyl]$_2$, P(4-methoxy-3,5-dimethylphenyl)$_2$ or P(C(CH$_3$)$_3$)$_2$
and
Ph denotes phenyl, o-, m- or p-methylphenyl or dimethylphenyl.

In the compounds of the formula A, $R^9$ and $R^{10}$ preferably denoted

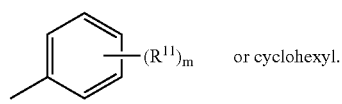

Particular preference is given to compounds of the formula A1

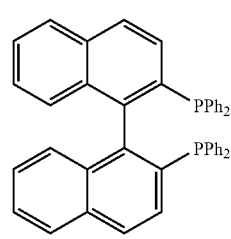

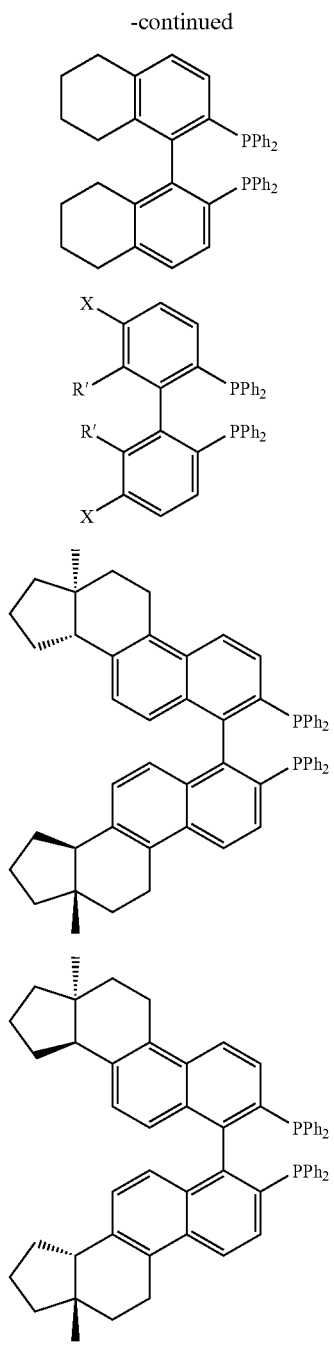

in which Ph has the meaning indicated above, and X denotes H, alkyl, O(alkyl), Cl, or F and R' denotes alkyl O(alkyl) or F. Particular preference is given to compounds of the formula A3 in which Ph denotes phenyl, X denotes H and R' denotes $OCH_3$.

Preferred compounds of the formula A are symmetrical.

The compounds of the formula II are preferably employed as acid-addition salts, where, in particular, the acid-addition salts of strong acids, such as, for example, hydrohalic acid, methyl-, p-toluene- or benzenesulfonic acid, perchloric, sulfuric or phosphoric acid, but also acetic acid, formic acid or propanoic acid, are suitable. Particular preference is given to acid-addition salts with sulfuric acid or the hydrochlorides of the compounds of the formula II. Use of the acid-addition salts of the compounds of the formula II gives the acid-addition salts of the compounds of the formula I, from which the free bases can be liberated by addition of a strong base, such as alkali metal carbonate or hydroxide.

The invention therefore relates, in particular, to a process for the preparation of the optically active forms, and the salts, hydrates and solvates, for example alcoholates, of the compounds of the formula I, in particular the compounds of the formula I in which n denotes 1.

The invention preferably facilitates the synthesis of optically active, aryl-substituted 3-monoalkylaminopropanols which are suitable as precursors in the preparation of antidepressants.

In particular, it opens up the possibility of obtaining enantiomerically pure or enantiomerically enriched (S)-3-methylamino-1-(2-thienyl)-1-propanol in a simple manner starting from 3-methylamino-1-(2-thienyl)-1-propanone. Likewise, enantiomerically pure or enantiomerically enriched (S)-3-methylamino-1-phenyl-1-propanol can be obtained in a simple manner starting from 3-methylamino-1-phenyl-1-propanone.

Cleavage of the racemic alcohol enables the desired enantiomer of 3-methylamino-1-(2-thienyl)-1-propanol to be obtained naturally in a maximum yield of 50% (for example analogously to Chirality 2000, 12, 26 or EP 650965).

J. Labelled Compd. Radiopharm. 1995, 36(3), 213 and Tetrahedron Lett. 1990, 31(49), 7101, describe the asymmetric synthesis of (S)-3-methylamino-1-(2-thienyl)-1-propanol. However, both synthetic routes require further transformations or the stoichiometric use of a chiral reagent. By contrast, the process according to the invention described here results in the desired enantiomer of the end product with high selectivity and yield without further transformations.

In general, the homogeneous hydrogenation of 3-aminoketones is regarded as problematical since in the majority of cases elimination products are obtained instead of the desired alcohol (J. Organomet. Chem. 1982, 232, C17 or Synlett, 1997, 1306). In the process according to the invention, this elimination proves to be unimportant (proportion of elimination product less than 2%).

Comparable processes for the preparation of 3-aminoalcohols are described in Synlett 1991, 689, but similar compounds are reduced to the corresponding alcohols with significantly worse enantioselectivities. Although the homogeneous ruthenium catalyst used in Org. Lett. 2000, 2(12), 1749, gives the alcohol in the hydrogenation of the 3-dimethyl-aminoketone with similarly good selectivities, a complex demethylation to be carried out subsequently is necessary to obtain the desired (S)-3-methylamino-1-(2-thienyl)-1-propanol or S)-3-methylamino-1-phenyl-1-propanol, in contrast to the process according to the invention. The formation of toxic and carcinogenic methyl chloride proves to be particularly disadvantageous here.

The invention therefore had the object of finding a process for the preparation of compounds which can be used, in particular, as intermediates in the synthesis of medicaments and which does not have the above-mentioned disadvantages.

It has been found that the compounds of the formula I and salts thereof which are important intermediates for the preparation of medicaments, in particular of those which exhibit, for example, actions on the central nervous system, can be obtained by enantioselective hydrogenation of compounds of the formula II in the presence of a chiral, non-racemic transition-metal catalyst.

Above and below, the radicals $R^1$, $R^2$, $R^3$, $R^4$, $R^5$, $R^6$, $R^7$, $R^8$, $R^9$, $R^{9'}$, $R^{10}$, $R^{11}$ and $R^{12}$, Q, Y and Z and the index m and n have the meanings indicated for the formulae I, II, A and B, unless expressly stated otherwise. If they occur more than once within a formula, the meanings of the individual radicals are independent of one another.

In the above formulae, alkyl has 1 to 20 C atoms, preferably 1 to 6, in particular 1, 2, 3 or 4 C atoms. Alkyl preferably denotes methyl or ethyl, furthermore propyl, isopropyl, furthermore also butyl, isobutyl, sec-butyl or tert-butyl.

$R^1$ is preferably an aromatic carbocyclic or heterocyclic radical which is unsubstituted or substituted by $R^3$ and/or $R^4$. This radical may be mono- or polycyclic and is preferably mono- or bicyclic, but in particular monocyclic. $R^1$ is particularly preferably unsubstituted.

If $R^1$ denotes a carbocyclic radical, this radical is preferably, for example, phenyl, o-, m- or p-tolyl, o-, m- or p-hydroxyphenyl, o-, m- or p-methoxyphenyl, o-, m- or p-fluorophenyl.

If $R^1$ denotes a heterocyclic radical, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo[1,4]oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, for example, are preferably suitable.

The heterocyclic radicals may also be partially or fully hydrogenated. The heterocyclic radical used can thus also be, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, 4- or -5-pyrrolyl, 2,5-dihydro-1-, -2-, -3-, 4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or 4-pyrazolyl, 1,4-dihydro-1-, -2-, -3- or -4-pyridyl, 1,2,3,4-tetrahydro-1-, -2-, -3-, -4-, -5- or-6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, 4- or-5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo[1,4]oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5-or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxo-furanyl.

The said heterocyclic radicals may additionally be substituted by $R^3$ and/or $R^4$.

$R^1$ particularly preferably denotes phenyl or 2-thienyl.

$R^2$ preferably denotes methyl, ethyl, n-propyl or isopropyl, but in particular methyl.

$R^3$ and $R^4$, independently of one another, denote H, methyl, in particular H.

$R^5$ and $R^6$ preferably denote H, alkyl, O-alkyl, Cl or F.

Preference is furthermore given to compounds of the formula A in which $R^5$ and $R^6$ together form a ring system.

$R^7$ and $R^8$ preferably denote H.

$R^{11}$ is preferably H or methyl, in particular methyl.

$R^{12}$ is preferably methyl or ethyl.

n is preferably 0 or 1, in particular 1.

m is preferably 1.

Aryloxy preferably denotes, for example, phenyloxy, o-, m- or p-tolyloxy, o-, m- or p-hydroxyphenyloxy, o-, m- or p-methoxyphenyloxy, o-, m- or p-fluorophenyloxy.

Aryl preferably denotes, for example, phenyl, o-, m- or p-tolyl, o-, m- or p-hydroxyphenyl, o-, m- or p-methoxyphenyl, o-, m- or p-fluorophenyl.

Preference is given to the use of the chiral ligands of the formula A.

Ph denotes phenyl, 2-, 3- or 4-methylphenyl, 2,3-, 2,4-, 2,5-, 2,6-, 3,4- or 3,5-dimethylphenyl.

Ph preferably denotes phenyl, 4-tolyl or 3,5-dimethylphenyl, where 4-tolyl is particularly preferred.

Y preferably denotes $P(C(CH_3)_3)_2$.

Z preferably denotes H.

Q preferably denotes $P(phenyl)_2$.

Preference is given to chiral ligands of the formula B in which Z has the meaning H and Y $P(C(CH_3)_3)_2$. Preference is furthermore given to ligands of the formula B in which Z has the meaning $P(phenyl)_2$ and Y has the meaning OH.

Preference is furthermore given to ligands of the formula B with the following combinations of the radicals Q and Y:

Q=$PPh_2$; Y=$P(cyclohexyl)_2$
Q=$PPh_2$; Y=$P(tert-butyl)_2$
Q=$P(cyclohexyl)_2$; Y=$P(cyclohexyl)_2$
Q=$PPh_2$; Y=$P(3,5-dimethylphenyl)_2$
Q=$P[3,5-bis(trifluoromethyl)phenyl]2$; Y=$P(cyclohexyl)_2$
Q=$P(4-methoxy-3,5-dimethylphenyl)_2$; Y=$P(3,5-dimethylphenyl)_2$
Q=$P[3,5-bis(trifluoromethyl)phenyl]2$; Y=$P(3,5-dimethylphenyl)_2$
Q=$P(cyclohexyl)_2$; Y=$P(tert-butyl)_2$
Q=$P(tert-butyl)_2$; Y=$P(3,5-dimethylphenyl)_2$ The process according to the invention is particularly suitable for the preparation of the alcohols (S)-3-methylamino-1-phenyl-1-propanol or (S)-3-methylamino-1-(2-thienyl)-1-propanol, which can advantageously be converted further into the active ingredients duloxetine, fluoxetine, tomoxetine and LY227942.

The compounds of the formula I have one or more chiral centres and can therefore occur in various stereoisomeric forms. The formula I encompasses all these forms.

The term "enantioselective preparation" defines a process which generally produces, as reaction product, a mixture comprising a compound of the formula IA

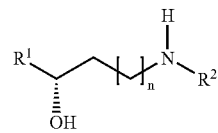

IA and a compound of the formula IB

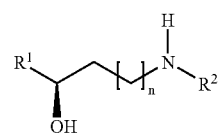

IB in which $R^1$, $R^2$ and n have the meaning indicated above, where this mixture is not racemic and preferably only still contains traces of the undesired enantiomer, depending on the chirality and selectivity of the catalyst used. In this case, reference is made above and below approximately to a process for the preparation of the enantiomerically pure compounds of the formula IA or IB. Processes for the preparation of the enantiomerically pure compounds of the formula IA are preferred.

In particular, it has been found that the compounds of the formula II can be hydrogenated using the enantiomerically pure rhodium-phosphine complexes containing the phosphines A or B to give enantiomerically pure or enantiomerically enriched compounds of the formula I.

The invention also relates to a process for the preparation of the compounds of the formula I, characterised in that the chiral, non-racemic catalyst is an enantiomerically enriched transition-metal complex containing one or more metals or salts thereof selected from the group consisting of rhodium, iridium, ruthenium and palladium. Particular preference is given to the use of transition-metal complexes containing rhodium or rhodium salts.

Particular preference is given to transition-metal salts containing sulfate, chloride, methanesulfonate, toluenesulfonate, hexachloroantimonate, hexafluoroantimonate or trifluoromethanesulfonate as anion.

Preference is given to the use of enantiomerically pure transition-metal complexes.

The term "enantiomerically pure" above and below denotes an enantiomeric purity of >90% ee, preferably >92% ee and in particular >99% ee.

Depending on the choice of the (R)- or (S)-enantiomer of the ligand in the catalyst, the (R)- or (S)-enantiomer is obtained in excess.

Particular preference is given to the ligands:

(S)-BINAP:

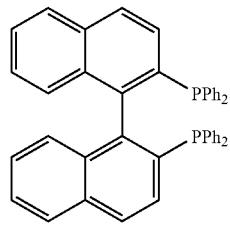

(S)-TolBINAP:

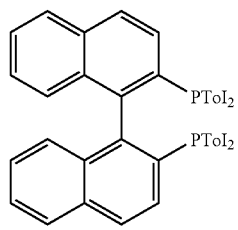

in which Tol denotes 4-methylphenyl. (S)-TolBINAP is particularly preferred.

The starting compound used for the preparation of the chiral complexes is preferably compounds such as, for example, [Rh(COD)$_2$]OTf (cyclooctadienylrhodium triflate), [Rh(COD)Cl]$_2$, [Rh(COD)$_2$]BF$_4$, [Ir(COD)Cl]$_2$, [Ir(COD)$_2$]BF$_4$, [Rh(NBD)Cl]$_2$ (norbornadienylrhodium chloride), [Rh(ethylene)$_2$Cl]$_2$, RhX$_3$·nH$_2$O, in which X denotes Cl, Br or I or [Ru(COD)Cl$_2$]$_x$. [Rh(COD)Cl]$_2$ is preferred.

Further preferred rhodium complexes contain one of the following anions

Cl, Br, I, PF$_6$, [PF$_3$(C$_2$F$_5$)$_3$], SbF$_6$, BF$_4$, ClO$_4$, BPh$_4$, tetra(3,5-bis-trifluoromethylphenyl)borate, OOCCH$_3$, OOCCF$_3$, OOCH, OOCCH$_2$CH$_3$, trifluoromethanesulfonate, p-toluenesulfonate, methanesulfonate and diethyl ether or one of the following unsaturated compounds:

1,5-cyclooctadiene, cyclooctene, 2,5-norbonadiene, norbornene.

The compounds of the formula II and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

If desired, the starting materials can also be formed in situ by not isolating them from the reaction mixture, but instead immediately converting them further into the compounds of the formula I.

Suitable solvents are, for example, water, hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as PEG, ethylene glycol monomethyl or monoethyl ether, ethylene glycol dimethyl ether (diglyme); ketones, such as acetone, methyl ethyl ketone or butanone; amides, such as acetamide, dimethylacetamide or dimethylformamide (DMF); nitriles, such as acetonitrile; sulfoxides, such as dimethyl sulfoxide (DMSO); carbon disulfide; nitro compounds, such as nitromethane or nitrobenzene; esters, such as methyl acetate or ethyl acetate, if desired also mixtures of the said solvents with one another or mixtures with water. Particular preference is given to mixtures of hydrocarbons with alcohols, in particular mixtures of methanol with toluene.

Particular preference is given to a process in which the hydrogenation is carried out in the presence of one or more alcohols, in particular methanol.

The reaction time of the enantioselective hydrogenation is between a few minutes and 14 days, depending on the conditions used, the reaction temperature is between 0 and 200° C., normally between 10 and 150° C., preferably between 20 and 130° C. and in particular between 20 and 70° C. The catalyst/substrate ratio is usually between 1:10,000 and 1:20, preferably between 1:5000 and 1:50, particularly preferably 1:2000 to 1:100. The reaction time is then, for example, between 0.1 and 30 preferably between 3 and 20 hours. The hydrogenation is preferably carried out under a hydrogen pressure of 1-250 bar, preferably at 3-210 bar, in particular between 120 and 200 bar.

The reactions are preferably carried out under oxygen-free reaction conditions.

For purification of the compounds of the formula I, it may be advantageous to follow the hydrogenation with crystallisation. In this case, in particular in the case where R$^1$ denotes 2-thienyl and R$^2$ denotes methyl, particularly high enantiomeric excesses are achieved without significant reductions in yield having to be accepted.

The invention furthermore relates to the use of the compounds of the formula I as intermediates for the synthesis of medicaments. Corresponding medicaments are mentioned, for example, in J. Labelled Compd. Radiopharm. 1995, 36(3), 213.

The invention furthermore relates to the use of the compounds of the formula I as intermediates for the synthesis of medicaments which exhibit actions on the central nervous system.

Above and below, all temperatures are indicated in ° C. and pressures in bar.

EXAMPLES

All reactions were carried out under inert conditions (i.e. anhydrous and oxygen-free reaction conditions).

1. Preparation of the Catalyst/Substrate Solution:

Example 1

51.4 mg of [Rh(COD)Cl]$_2$ were dissolved in 5 ml of the solvent mixture toluene, and a solution consisting of 5 ml of toluene and equivalents 1.1 of (S)-(−)-2,2'bis(di-p-tolylphosphino)-1,1'-binaphthyl was added.

2. Sampling and Analysis

The enantiomeric excess of the hydrogenation product was determined on chiral HPLC phase.

Example 2

5.3 mg of bis(1,5-cyclooctadienyl)dirhodium(I) dichloride and 17.2 mg of (S)-(−)-2,2'bis(di-p-tolylphosphino)-1,1'-binaphthyl are added to 8.23 g of 3-methylamino-1-(2-thienyl)-1-propanone in a steel autoclave, and 50 ml of methanol and 50 ml of toluene are added to this mixture. After the reactor has been sealed, the reactor is freed from oxygen by flushing a number of times with nitrogen and subsequently hydrogen. The reactor is charged with 55 bar of hydrogen and warmed to 50° C. The course of the reaction is monitored through the pressure drop in the autoclave. The reaction is complete after 15 hours.

The desired alcohol is obtained with an enantiomeric excess of 92.8% ee.

Example 3

The oily residue obtained in accordance with Example 2 is taken up in 300 ml of water, extracted 3 times with 250 ml of dichloromethane each time, and the organic phase is discarded. 250 ml of dichloromethane are subsequently again added to the aqueous phase, the pH is adjusted to 14 using 41.0 g of 32% sodium hydroxide solution, and the phases are separated. The organic phase is freed from the solvent. The oil obtained is dissolved in 320 g of an MTB ether/toluene mixture at 55° C., 2.5 g of activated carbon are added, and the mixture is filtered while hot. After the virtually colourless solution has been slowly cooled to room temperature, the reaction solution is seeded with a few seed crystals and cooled at −15° C. for 16 h. The deposited crystals are filtered off with suction and dried in vacuo, giving the desired (S)-N-methyl-3-hydroxy-3-(2-thienyl)propanamine with an ee value of >99%.

Example 4

18.93 g (92 mmol) of 3-methylamino-1-(2-thienyl)-1-propanone are weighed out into a steel autoclave, 90 ml of methanol are added, and the mixture is inertised by injecting 7 bar of nitrogen 3 times followed by decompression. 10.8 mg (0.022 mmol) of bis(1,5-cyclooctadienyl)dirhodium(I) dichloride and 32.5 mg (0.051 mmol) of (S)-BINAP are weighed out into a Schlenk tube and dissolved in 18 ml of toluene under argon. This solution is transferred into the autoclave using a cannula in a counterstream of nitrogen. The autoclave is then flushed by charging 3 times with 10 bar of hydrogen each time followed by decompression.

The autoclave is heated to 50° C., and the internal pressure is adjusted to 120 bar of hydrogen after this temperature has been reached. After 7 hours, the uptake of hydrogen ceases, the reaction is terminated, and the reaction solution is analysed.

Conversion to the product: 98%; enantiomeric excess in the product: 94%.

Example 5

495 g (2.4 mol) of 3-methylamino-1-(2-thienyl)-1-propanone are weighed out into a steel autoclave, 2.3 l of methanol and 0.4 l of toluene are added, and the mixture is inertised by injecting 7 bar of nitrogen 3 times followed by decompression. 297 mg (0.60 mmol) of bis(1,5-cyclooctadienyl)-dirhodium(I) dichloride and 900 mg (1.325 mmol) of (S)-TolBINAP are weighed out into a Schlenk flask and dissolved in 80 ml of toluene under argon. This solution is transferred into the autoclave using a cannula in a counterstream of nitrogen. The autoclave is then flushed by charging 3 times with 10 bar of hydrogen each time followed by decompression.

The autoclave is heated to 50° C., and the internal pressure is adjusted to 60 bar of hydrogen after this temperature has been reached. After 8 hours, the uptake of hydrogen ceases, the reaction is terminated, and the reaction solution is analysed.

Conversion to the product: >99%; enantiomeric excess in the product: 92%.

Example 6

16.46 g (80 mmol) of 3-methylamino-1-(2-thienyl)-1-propanone are weighed out into a steel autoclave, 75 ml of methanol are added, and the mixture is inertised by injecting 7 bar of nitrogen 3 times followed by decompression. 5.2 mg (0.011 mmol) of bis(1,5-cyclooctadienyl)-dirhodium(I) dichloride and 15.2 mg (0.022 mmol) of (S)-TolBINAP are weighed out into a Schlenk tube and dissolved in 15 ml of toluene under argon. This solution is transferred into the autoclave using a cannula in a counterstream of nitrogen. The autoclave is then flushed by charging 3 times with 10 bar of hydrogen each time followed by decompression. The autoclave is heated to 50° C., and the internal pressure is adjusted to 120 bar of hydrogen after this temperature has been reached. After 11 hours, the uptake of hydrogen ceases, the reaction is terminated, and the reaction solution is analysed.

Conversion to the product: >99%; enantiomeric excess in the product: 92%.

The invention claimed is:

1. A process for the enantioselective preparation of amino alcohols of the formula I

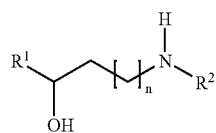

in which
R$^1$ denotes a saturated, unsaturated or aromatic carbocyclic or heterocyclic radical which is unsubstituted or mono- or polysubstituted by R$^3$ and/or R$^4$,
R$^2$ denotes alkyl having 1-20 C atoms or H,
R$^3$, R$^4$ each, independently of one another, denote H, alkyl or alkoxy having 1-20 C atoms, aryl, aryloxy or COOR$^2$, F, Cl, Br, OH, CN, NO$_2$, N(R$^2$)$_2$ or NHCOR$^2$ and
n denotes 0, 1, 2 or 3,
by enantioselective hydrogenation of amino ketones of the formula II

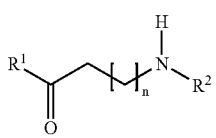

in which
R$^1$, R$^2$ and n have the meaning indicated above, in the presence of a non-racemic catalyst, wherein the catalyst is a transition-metal complex in which the transition metal is complexed to a chiral diphosphine ligand A

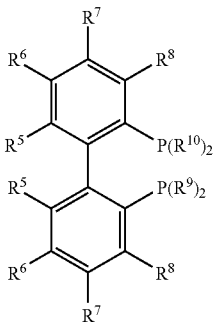

in which
R$^5$, R$^6$, R$^7$ and R$^8$ each, independently of one another, denote H, alkyl or alkoxy having 1-20 C atoms, aryl, aryloxy or F, Cl, Br, N(R$^2$)$_2$ or NHCOR$^2$
each, independently of one another, denote
R$^9$ and R$^{10}$

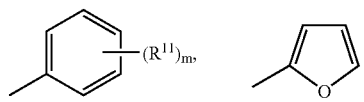

or cyclohexyl

R$^{11}$ denotes H, alkyl or alkoxy having 1-20 C atoms, aryl, aryloxy or SO$_3$Na, COOR$^{12}$, F, Cl, N(R$^{12}$)$_2$ or NHCOR$^{12}$,
R$^{12}$ denotes alkyl having 1-20 C atoms or H and
m denotes 0, 1, 2 or 3,
where R$^5$ and R$^6$, R$^6$ and R$^7$ and R$^7$ and R$^8$ together can also have the meaning

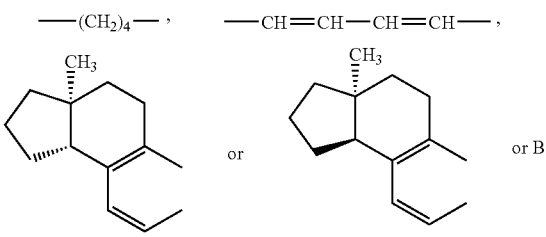

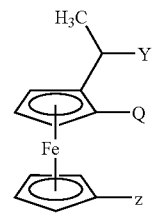

in which
Y denotes OH, P(cyclohexyl)$_2$, P(3,5-dimethylphenyl)$_2$ or P(C(CH$_3$)$_3$)$_2$,
Z denotes H or P(phenyl)$_2$,
Q denotes PPh$_2$, P(cyclohexyl)$_2$, P[3,5-bis(trifluoromethyl)phenyl]$_2$, P(4-methoxy-3,5-dimethylphenyl)$_2$ or P(C(CH$_3$)$_3$)$_2$ and
Ph denotes phenyl, o-, m- or p-methylphenyl or dimethylphenyl and
wherein the reaction time of the enantioselective hydrogenation is from 0.1 to 30 hours.

2. A process according to claim 1, in which R$^1$ denotes phenyl or 2-thienyl.

3. A process according to claim 1, in which R$^2$ denotes methyl, ethyl, n-propyl or isopropyl.

4. A process according to claim 1, in which n denotes 1.

5. A process according to claim 1 for the preparation of (S)-3-methylamino-1-phenyl-1-propanol or (S)-3-methylamino-1-(2-thienyl)-1-propanol or acid-addition salts thereof.

6. A process for the preparation of a compound according to claim 1, wherein the chiral, non-racemic catalyst is a transition-metal complex containing one or more metals or salts thereof selected from the group consisting of rhodium, iridium, ruthenium and palladium.

7. A process for the preparation of a compound according to claim 1, wherein the chiral, non-racemic catalyst is a transition-metal complex containing rhodium or salts thereof.

8. A process according to claim 1, wherein the chiral diphosphine ligand used is a compound of the formula A1 to A5:

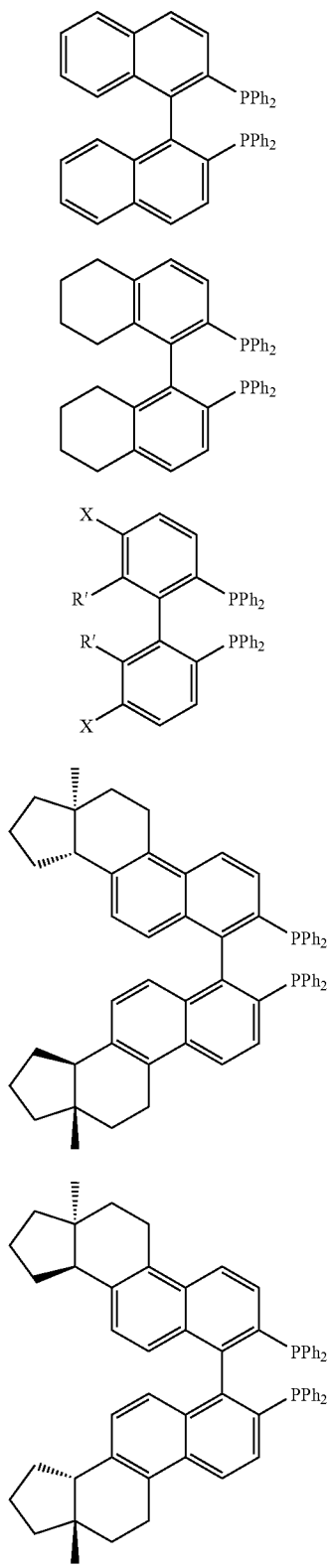

A1

A2

A3

A4

A5 in which Ph has the meaning indicated in claim 1, and X denotes H, alkyl, O(alkyl), Cl, or F, and R' denotes alkyl O(alkyl) or F.

9. A process according to claim 7, wherein the chiral diphosphine ligand used is (S)-(−)-2,2'bis(di-p-tolylphosphino)-1,1'-binaphthyl or (S)-(−)-2,2'bis(diphenylphosphino)-1,1'-binaphthyl.

10. A process for the preparation of a compound according to claim 1, wherein the reaction temperature is between 0 and 200° C.

11. A process for the preparation of a compound according to claim 1, wherein the catalyst/substrate ratio is between 1:5000 and 1:50.

12. A process for the preparation of a compound according to claim 1, wherein the hydrogenation is carried out under 1-200 bar of hydrogen.

13. A process for the preparation of a compound according to claim 1, wherein the hydrogenation is carried out in the presence of an alcohol.

14. A process for the preparation of a compound according to claim 1, wherein the chiral, non-racemic catalyst is a transition-metal complex containing sulfate, chloride, bromide, iodide, $PF_6$, $BF_4$, methanesulfonate, toluenesulfonate, hexachloroantimonate, hexafluoroantimonate or trifluoromethanesulfonate as anion.

15. A process for the preparation of a compound according to claim 1, wherein n=2.

16. A process according to claim 1, where in n=3.

17. A process for the preparation of a compound according to claim 1, wherein said compound is obtained in an enantiomeric excess of at least 92.8%.

18. A process for the preparation of a compound according to claim 1, wherein $R^3$ and $R^4$, independently of one another are H or methyl.

19. A process for the preparation of a compound according to claim 1, wherein $R^5$ and $R^6$ independently of one another are H, alkyl, O-alkyl, Cl, F or in which $R^5$ and $R^6$ together form a ring system.

20. A process for the preparation of a compound according to claim 1, wherein $R^7$ and $R^8$ are H.

21. A process for the preparation of a compound according to claim 1, wherein $R^{11}$ is H or methyl.

22. A process for the preparation of a compound according to claim 1, wherein $R^{12}$ is methyl or ethyl.

23. A process for the preparation of a compound according to claim 1, wherein in is 1.

24. A process for the enantioselective preparation of amino alcohols of formula I

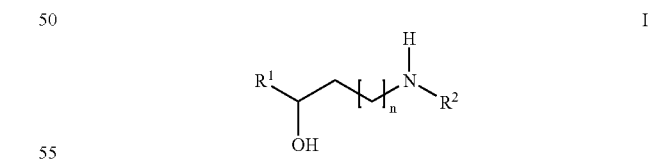

in which
$R^1$ denotes a heterocyclic radical which is unsubstituted or mono- or polysubstituted by $R^3$ and/or $R^4$,
$R^2$ denotes methyl
$R^3$, $R^4$ each, independently of one another, denote H, alkyl or alkoxy having 1-20 C atoms, aryl, aryloxy or $COOR^2$, F, Cl, Br, OH, CN, $NO_2$, $N(R^2)_2$ or $NHCOR_2$ and
n denotes 1,2 or 3,
by enantioselective hydrogenation of amino ketones of the formula II

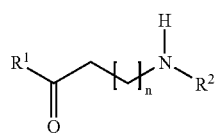

in which
R¹, R² and n have the meaning indicated above, in the presence of a non-racemic catalyst, wherein the catalyst is a transition-metal complex in which the transition metal is complexed to a chiral diphosphine ligand A

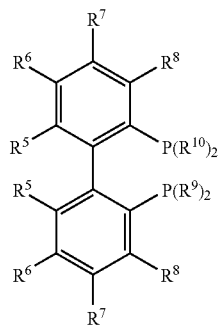

in which
$R^5$, $R^6$, $R^7$ and $R^8$ each, independently of one another, denote H, alkyl or alkoxy having 1-20 C atoms, aryl, aryloxy or F, Cl, Br, $N(R^2)_2$ or $NHCOR^2$
each, independently of one another, denote
$R^9$ and $R^{10}$

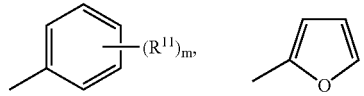

or cyclohexyl
$R^{11}$ denotes H, alkyl or alkoxy having 1-20 C atoms, aryl, aryloxy or $SO_3Na$, $COOR^{12}$, F, Cl, $N(R^{12})_2$ or $NHCOR^{12}$, $R^{12}$ denotes alkyl having 1-20 C atoms or H and
m denotes 0, 1, 2 or 3,
where $R^5$ and $R^6$, $R^6$ and $R^7$ and $R^7$ and $R^8$ together can also have the meaning

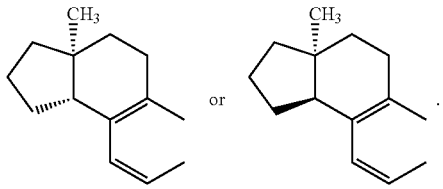

25. A process according to claim 24, wherein said ligand A is

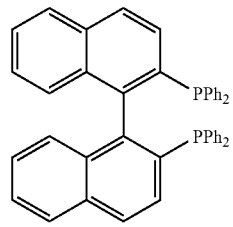

wherein Ph denotes methylphenyl.

26. A process according to claim 4, wherein said ligand A is

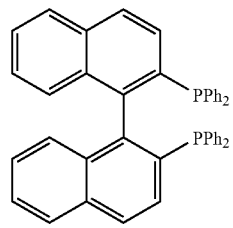

wherein Ph denotes methylphenyl.

* * * * *

UNITED STATES PATENT AND TRADEMARK OFFICE
CERTIFICATE OF CORRECTION

PATENT NO.       : 7,488,833 B2
APPLICATION NO.  : 10/525821
DATED            : February 10, 2009
INVENTOR(S)      : Kralik et al.

Page 1 of 1

It is certified that error appears in the above-identified patent and that said Letters Patent is hereby corrected as shown below:

Column 11, line 20 reads "n denotes 0, 1, 2, or 3," should read --n denotes 1, 2, or 3,--

Signed and Sealed this

Fifth Day of May, 2009

JOHN DOLL
*Acting Director of the United States Patent and Trademark Office*